United States Patent [19]

Fuchs et al.

[11] Patent Number: 5,700,358
[45] Date of Patent: Dec. 23, 1997

[54] RECOVERY OF CAPROLACTAM FROM OLIGOMERS AND/OR POLYMERS OF CAPROLACTAM

[75] Inventors: Hugo Fuchs; Josef Ritz, both of Ludwigshafen; Gerald Neubauer, Weinheim, all of Germany

[73] Assignee: BASF Aktiengesellschaft, Ludwigshafen, Germany

[21] Appl. No.: 396,623

[22] Filed: Mar. 1, 1995

[30] Foreign Application Priority Data

Mar. 4, 1994 [DE] Germany ............. 44 07 222.8

[51] Int. Cl.$^6$ ............. B01D 3/34; C07D 201/16
[52] U.S. Cl. ............. 203/31; 203/35; 203/37; 203/74; 203/75; 203/78; 540/540
[58] Field of Search ............. 203/34, 35, 31, 203/36–37, DIG. 16, 14, 74, 75, 78; 540/540; 210/758, 766, 767

[56] References Cited

U.S. PATENT DOCUMENTS

| | | | |
|---|---|---|---|
| 3,182,055 | 5/1965 | Bonfeld et al. | |
| 3,264,060 | 8/1966 | Nieswandt et al. | |
| 3,600,381 | 8/1971 | Yamamoto et al. | 540/540 |
| 4,457,807 | 7/1984 | Rulkens et al. | 203/89 |
| 4,720,328 | 1/1988 | Corbin et al. | 203/37 |
| 4,795,571 | 1/1989 | Holzknecht et al. | |
| 4,892,624 | 1/1990 | Fuchs | 203/70 |
| 5,458,740 | 10/1995 | Losier et al. | 159/47.3 |

FOREIGN PATENT DOCUMENTS

| | | |
|---|---|---|
| 279 439 | 8/1988 | European Pat. Off. |
| 522235 | 1/1993 | European Pat. Off. |
| 739953 | 5/1943 | Germany. |
| 5310 | 6/1953 | Germany. |
| 950 726 | 9/1956 | Germany. |
| 1 194 863 | 2/1966 | Germany. |
| 1 272 297 | 7/1968 | Germany. |
| 31 06 350 | 12/1981 | Germany. |
| 2 072 025 | 8/1981 | United Kingdom. |

OTHER PUBLICATIONS

Database WPI, Week 8651, Derwent Publications Ltd., AN 86–338250 (English abstract of SU–A 1 231 052).
Pat. Abst. of Japan, vol. 3, o. 128 (C–62), Oct. 24, 1979 (English abstract of JP–A 54 109992).
Pat. Abst. of Japan, vol. 7, No. 7 (C–144), Jan. 12, 1983 (English abstract of JP–A 57 165364).
Pat. Abst. of Japan, vol. 2,, No. 93 (C–78), Jul. 29, 1978 (English abstract of JP–A 53 053686).

Primary Examiner—Virginia Manoharan
Attorney, Agent, or Firm—Keil & Weinkauf

[57] ABSTRACT

Caprolactam is recovered from oligomers and/or polymers of caprolactam by cleavage of oligomers and/or polymers of caprolactam and subsequent working up by distillation of the caprolactam obtained in the cleavage, by a process including (a) cleaving oligomers and/or polymers of caprolactam to obtain an aqueous reaction mixture which contains caprolactam, (b) removing water from the reaction mixture obtained under (a) to obtain a residue, (c) distilling the residue obtained under (b) in an acidic medium and (d) then distilling the distillate in an alkaline medium to obtain caprolactam, or (c') distilling the residue obtained under (b) in an alkaline medium and (d') then distilling the distillate in an acidic medium to obtain caprolactam.

6 Claims, No Drawings

RECOVERY OF CAPROLACTAM FROM OLIGOMERS AND/OR POLYMERS OF CAPROLACTAM

The present invention relates to a process for recovering caprolactam from oligomers and/or polymers of caprolactam by cleavage of oligomers and/or polymers of caprolactam and subsequent working up by distillation of the caprolactam obtained in the cleavage.

In the preparation of polycaprolactam and in the processing thereof to give moldings, Such as filaments, fibers, films or injected molded or extruded articles, oligomers of caprolactam and polycaprolactam wastes are obtained and have to be disposed of. The consumer goods produced from polycaprolactam, such as films, fabrics, packaging and shaped articles, likewise finally have to be disposed of. The recovery of caprolactam from polycaprolactam is possible in this procedure.

Polycaprolactam can be cleaved to caprolactam in an acidic or alkaline medium. The cleavage described in DE-A 950 726 and effected by means of phosphoric acid has the disadvantage that products containing phosphoric acid are obtained and are expensive to dispose of in an environment-friendly manner. The cleavage described in DD-A 5310 and effected by means of sodium hydroxide has the disadvantage that the caprolactam obtained is generally of poor quality and therefore has to be purified by an expensive procedure in order to make it suitable for further processing.

It is an object of the present invention to provide a process for recovering caprolactam by cleaving oligomers and/or polymers of caprolactam, in which the byproducts are converted into useful products.

We have found that this object is achieved by a process for recovering caprolactam from oligomers and/or polymers of caprolactam by cleavage of oligomers and/or polymers of caprolactam and subsequent working up by distillation of the caprolactam obtained in the cleavage, which comprises (a) cleaving oligomers and/or polymers of caprolactam to obtain an aqueous reaction mixture which contains caprolactam, (b) removing water from the reaction mixture obtained under (a) to obtain a residue, (c) distilling the residue obtained under (b) in an acidic medium and (d) then distilling the distillate in an alkaline medium to obtain caprolactam, or (c') distilling the residue obtained under (b) in an alkaline medium and (d') then distilling the distillate in an acidic medium to obtain caprolactam.

The cleavage of oligomers and/or polymers of caprolactam can be carried out by various methods. For example, according to DE-A 950 726 or DE-A 12 72 297, polycaprolactam can be cleaved at from 200° to 400° C. in the presence of a nonvolatile acid, such as phosphoric acid, to give caprolactam, and the resulting caprolactam can be distilled off from the reaction mixture by means of superheated steam.

According to DD-A 5310, the cleavage may also be carried out in the presence of potassium hydroxide at above 250° C. at below 20 mmHg.

In a particular embodiment, from 5 to 50, in particular from 10 to 20, parts by weight of water are used per part by weight of oligomers and/or polymers of caprolactam, and the reaction is carried out in general at from 200° to 350° C., advantageously from 210° to 300° C. Furthermore, the cleavage is carried out, as a rule, under superatmospheric pressure, for example from 20 to 200, in particular from 20 to 100, bar. It has proven useful to increase the pressure by forcing in an inert gas, such as nitrogen. Advantageously, the pressure and temperature conditions are tailored to one another so that a liquid phase is present.

As a rule, residence times of from 3 to 6 hours are maintained during the cleavage. It has proven useful to cleave at least 60, in particular 60 to 90%, by weight of the caprolactam oligomer and/or polymer used into caprolactam.

An essential feature of this embodiment is that the cleavage is carried out in the presence of an alkali metal hydroxide, such as potassium hydroxide or in particular sodium hydroxide, at a pH of up to 10, particularly preferably from 6 to 8.

After the pressure has been let down, an aqueous solution or suspension which contains monomeric caprolactam, oligomers thereof and possibly unhydrolyzed polycaprolactam is usually obtained.

In a further preferred embodiment for cleaving polycaprolactam, oligomers and/or polymers of caprolactam are first hydrolytically cleaved, in general with from 1 to 20, in particular from 2 to 10, parts by weight of water per part by weight of polycaprolactam. As a rule, a temperature of from 200° to 350° C., in particular from 250° to 300° C., is maintained in this procedure. The treatment is usually carried out under superatmospheric pressure, advantageously at from 15 to 200 bar, the superatmospheric pressure additionally being generated by forcing in an inert gas, such as nitrogen. Of course, a liquid aqueous phase is maintained. The treatment is carried out in general using a residence time of from 0.5 to 10, in particular from 1 to 5, hours. It has also proven useful additionally to use alkali metal hydroxides, in particular sodium hydroxide, in an amount of from 0.001 to 0.1 part by weight per part by weight of oligomer and/or polymer of caprolactam.

In general, an aqueous reaction mixture which contains polycaprolactam, monomeric caprolactam and oligomers thereof is obtained. A typical composition is, for example, from 1 to 70% by weight of caprolactam, from 0.1 to 10% by weight of oligomers of caprolactam and from 1 to 99% by weight of suspended polycaprolactam, the percentages being based on polycaprolactam used.

The reaction mixture thus obtained is usually then passed into a fluidized alumina bed at from 270° to 400° C., a mixture of steam and caprolactam being obtained.

Before being introduced into the fluidized bed, the reaction mixture may be let down, but it is advantageously introduced into the fluidized bed via a nozzle orifice directly while letting down the pressure. Introduction into the fluidized bed may also be effected by blowing in by means of a nozzle operated with an inert gas.

Suitable aluminas are the various modifications, such as clay, boehmite or α- or γ-alumina. γ-Alumina has proven a particularly useful catalyst. The catalyst is kept fluidized by means of an inert gas, such as carbon dioxide, argon or nitrogen, preferably nitrogen. Alumina having particle sizes of from 0.05 to 1.5 mm, in particular from 0.1 to 0.4 mm, is advantageously used. The height of the fluidized bed is advantageously chosen so that the residence time of the oligomer and polymeric caprolactam in the catalyst bed is from 0.1 to 30, in particular from 0.5 to 10, seconds. The treatment in the fluidized bed is advantageously carried out at atmospheric pressure. However, slightly reduced or slightly superatmospheric pressure, for example from 0.5 to 2 bar, may also be used.

A temperature of from 290° to 360° C. is advantageously maintained in the fluidized bed. It is therefore also advantageous to feed the inert gas at from 290° to 400° C. into the fluidized bed.

The condensable fractions are separated off by condensation from the gas mixture emerging from the fluidized bed and are then worked up by distillation.

According to the invention, the starting material comprises oligomers and/or polymers of caprolactam which are to be disposed of, for example wastes which are obtained in the preparation of polycaprolactam or the processing thereof to give filaments, films or injection molded or extruded parts, as well as shaped consumer goods, such as films, packaging, fabrics, filaments and extruded parts, which are to be disposed of. The polycaprolactam articles to be cleaved are advantageously comminuted prior to cleavage, for example by milling, and if necessary compacted beforehand. Polycaprolactam having a particle size of from 1 to 100 mm is advantageously used as the starting material.

According to the invention, water is removed by a method known per se, such as distillation or extraction, preferably distillation, from the aqueous reaction mixture obtained after the cleavage. The water removed, which usually contains steam-volatile impurities, is preferably fed to a biological waste water treatment.

In a further preferred embodiment, the aqueous reaction mixture obtained after the cleavage is treated with lime, conventional oxidizing agents, such as potassium permanganate, and/or active carbon, in a manner known per se, prior to removal of water. The total amount of lime, oxidizing agents and active carbon depends essentially on the amount of impurities present in the reaction mixture and is, as a rule, from 0 to 5, preferably from 0.01 to 1%, by weight, based on the aqueous reaction mixture.

After this treatment, the solid component is usually removed in a manner known per se, for example by filtration or centrifuging, preferably by filtration, and removal of water is then effected by one of the abovementioned methods.

The residue obtained after removal of water and, if required, after treatment with lime, oxidizing agents and/or active carbon is fed, according to the invention, to a distillation. For this purpose, an acid or an acidic ion exchanger is added to the residue from reaction stage (b).

Suitable acids are usually mineral acids, such as sulfuric acid, oleum or phosphoric acid, and organic acids, such as p-toluene-sulfonic acid, preferably sulfuric acid.

For example, commercial ion exchangers, such as crosslinked polystyrene having sulfo groups as active groups, can be used as the acidic ion exchangers.

The amount of acid is generally chosen to be from 0.01 to 5, preferably from 0.1 to 1%, by weight, based on caprolactam. The amount of ion exchanger is chosen as a rule to be from 1 to 30, preferably from 2 to 10%, by weight, based on caprolactam.

The distillation is usually carried out at reduced pressure, ie. at less than 100 kPa, preferably from 300 to 2000 Pa. The temperature is chosen as a rule to be from 100° to 180° C., preferably from 120° to 150° C.

In a preferred embodiment, the forerunnings, which essentially contain low boilers, such as aniline and/or aliphatic amides, are worked up separately, preferably together with the forerunnings from the distillation in the alkaline medium (see below). For this purpose, the forerunnings obtained in the distillation in the acidic and/or basic medium are preferably fed to a separate, conventional distillation column. A reflux ratio of from 1 to 30, in particular from 5 to 20, is particularly advantageously employed, as a rule from 0.1 to 20, preferably from 0.5 to 10%, by weight of the amount used being obtained as distillate. The bottom temperature is preferably chosen to be from 130° to 160° C., and the procedure is carried out at from 400 to 600 Pa.

The distillate obtained is usually fed to an incineration plant, energy being recovered. The bottom product of the distillation is advantageously fed to the distillation stage in the acidic medium.

The distillation residue obtained in the distillation in the acidic medium is fed, according to the invention, to a cleavage sulfuric acid plant if sulfuric acid is used in the distillation, for incineration with recovery of sulfur dioxide. Advantageously, the distillation residue can be fed together with extraction water (raffinate), as obtained from caprolactam preparation by Beckmann rearrangement of cyclohexanone oxime (cf. for example DE-A 11 94 863), for incineration in a cleavage sulfuric acid plant.

The distillate from distillation in the acidic medium is usually taken off at a boiling point of from 110° to 130° C. and fed to further distillation, in an alkaline medium. The amounts of distillate are as a rule from 1 to 10% by weight, based on the dewatered residue used.

The distillation in the alkaline medium is carried out, for example, as in the method described in DE-A 31 06 350, an alkali metal hydroxide, such as sodium hydroxide or potassium hydroxide, preferably the former, being added to the material to be distilled, in an amount of from 0.01 to 1, preferably from 0.01 to 0.5%, by weight, based on the material to be distilled.

The pressure during the distillation is chosen to be from 50 to 3000, preferably from 100 to 2000, Pa. The distillate is as a rule taken off at a boiling point of from 110° to 130° C.

In a preferred embodiment, the forerunnings which were obtained in the distillation in the alkaline medium and essentially contain low boilers, such as amines, aliphatic amides and nitriles, are worked up separately, preferably together with the forerunnings from the distillation in the acidic medium. The procedure corresponds to that described for working up the forerunnings from the distillation in the acidic medium. The distillate obtained here is usually fed to an incineration plant, energy being recovered. The bottom product of the distillation, usually containing essentially caprolactam and methylcaprolactam, is advantageously fed to the distillation stage in the acidic medium.

In a preferred embodiment, the residues of the distillation in the alkaline medium are worked up by distillation. For this purpose, they are distilled in a distillation column usually provided with packings, for example Sulzer packings, Pall rings or Raschig rings, at, preferably, from 300 to 1000 Pa and a bottom temperature of up to 160° C. The distillation column is advantageously operated under a gentle reflux. However, the distillation can also be be carried out, for example, in a thin-film evaporator. The distillate of this working-up stage is advantageously fed to the distillation in the acidic medium, and the distillation residues which contain essentially alkali metal compounds are preferably fed to an incineration plant. The incineration generally gives sodium carbonate as a desired product and useful heat energy.

The distillate obtained in the distillation in the alkaline medium consists in general of from 98 to 99.9% by weight of caprolactam.

If further purification of the caprolactam thus obtained appears necessary, it can be achieved by known methods, such as crystallization (cf. EP-A-279 439) and/or by mixing the caprolactam obtained according to the invention with caprolactam from the Beckmann rearrangement and carrying out conventional further purification together.

Furthermore, observations to date have shown that it is of minor importance whether the dewatered reaction mixture from the cleavage of oligomeric caprolactamor polycaprolactamis fed first to the distillation in the acidic medium and then to the distillation in the alkaline medium, or conversely.

The novel process for cleaving and working up polycaprolactam permits reutilization and/or controlled disposal of all residues and gives caprolactam in a purity as required for the polymerization of caprolactam. The novel process is therefore environment-friendly and saves raw material. It is therefore suitable for the disposal of materials containing oligomers and/or polymers of caprolactam, such as carpets, sinks, bristles and other commercial molding materials based on polycaprolactam.

EXAMPLE 1

10,000 g of dewatered caprolactam from a cleavage plant were distilled with 0.3% by weight of sulfuric acid in a column filled with Raschig rings, at 500 Pa. The caprolactam used was composed of 7787 g of caprolactam from a cleavage plant, 1263 g of caprolactam obtained from the bottom of a column for separating off high boilers and 950 g of caprolactam obtained from a column for separating off low boilers.

In this distillation in an acidic medium, 600 g of distillate were taken off as forerunnings. The amount of residue obtained was 300 g. This was incinerated with recovery of $SO_2$.

The main amount of the distillation in the acidic medium (9100 g) was distilled in a second column containing Sulzer packings, with the addition of 0.25 % by weight of sodium hydroxide. The distillation was carried out at 500 Pa and a bottom temperature of 130° C. In this distillation, 455 g of distillate were taken off as forerunnings. The forerunnings of the distillation in the acidic and in the alkaline medium were distilled together in a column at a reflux ratio of 20 and at 500 Pa. Once again, forerunnings comprising about 10% by weight, based on the amount used, were taken off and incinerated. The bottom product of this forerunnings distillation (950 g) was once again fed to the distillation in the acidic medium.

The main product of the second distillation carried out under alkaline conditions (7280 g) consisted of caprolactam defined as pure lactam and having the following quality characteristics:

| | |
|---|---|
| Permanganate absorption number[1] | 3.6 |
| Absorbance [1 cm cell/290 nm] of a 50% strength by weight aqueous solution | 0.028 |
| Free bases [meq/kg] | 0.01 |
| Volatile bases [meq/kg] | 0.29 |
| Octahydrophenazine [mg/kg] | 0.5 |
| APHA color number | <1 |

[1] also see caprolactam brochure from BASF or caprolactam ISO standards

The 1365 g of bottom product obtained in the second distillation carried out under alkaline conditions were in turn worked up at 500 Pa by distillation. A residue of 102 g contained the total amount of NaOH added and was incinerated with recovery of sodium carbonate. The distillate of 1263 g was fed to the distillation in the acidic medium (see above).

For the photometric determination of the permanganate absorption number, 1,000 g of the mixture to be investigated was introduced in each case into a 100 ml volumetric flask.

Thereafter, distilled oxygen-free water having a pH of 6.2–6.5 was added up to the calibration mark and the contents were thoroughly mixed. A second 100 ml volumetric flask was made up to the calibration mark only with distilled oxygen-free water having a pH of 6.2–6.5. After both flasks had been thermostated at 25° C. (about 30 minutes), 2.00 ml of a 0.01N potassium permanganate solution were added first to the water and immediately thereafter to the caprolactam-containing solution. At the beginning of the potassium permanganate addition, a stopwatch was started. Both flasks were immediately closed and the contents thoroughly mixed, and the flasks were placed in the thermostat again. After about 9 minutes, two cells having a length 1 of 5 cm were filled with the two solutions and placed in a spectrophotometer. 10 minutes ±10 seconds after the addition of potassium permanganate solution, the absorbance A at 420 nm of the caprolactam solution was measured against the permanganate-treated water. The permanganate absorption number is then obtained from the difference between the absorbances of the two solutions, multiplied by the factor 100.

The content of volatile bases was determined by the Kjeldahl method in an apparatus according to Parnas. For this purpose, 100 ml of 4 mol/l sodium hydroxide solution were introduced per measurement into the Kjeldahl flasks of the apparatus, and 20±0.1 g of the solution to be investigated, with a total of 70 ml of distilled water, were added. 50 ml of the flask contents were then distilled in the course of about 5 minutes, while blowing steam through the solution in the Kjeldahl flask, into a receiver which contained 5.00 ml of 0.02 mol/1 hydrochloric acid, 30 ml of distilled water and 5 drops of an indicator solution (prepared from 0.3 g of methyl red and 0.3 g of methylene blue in 400 ml of methanol). The excess of hydrochloric acid in the receiver was back-titrated with 0.02 mol/l sodium hydroxide solution (consumption: A ml). A blank value determination without the addition of a caprolactam solution gave the content of volatile bases in the sodium hydroxide solution used (consumption: B ml). The content of volatile bases was then calculated as (B−A)·0.02·1000/20=B−A meq/kg.

The APHA color number was determined by measuring the absorbance A of 50% (m/m) aqueous caprolactam solution at a wavelength $\lambda=390$ nm in a cell having a length 1 of 5 cm and expressing it in Hazen units (platinum-cobalt scale). For this purpose, the measured absorbance A was multiplied by the factor f=150.

Hazen color number (platinum-cobalt scale): the unit is defined as the color of a solution which contains 1 mg of platinum in one liter of water in the form of hexachloroplatinic(IV) acid in the presence of 2 mg of cobalt(II) chloride hexahydrate.

The Hazen units correspond to the APHA units.
Preparation of the standard solution corresponding to 500 Hazen units:

1.000 g of cobalt(II) chloride hexahydrate ($COCl_2 \cdot 6\ H_2O$) and 1.245 g of potassium hexachloroplatinate(IV) ($K_2PtCl_6$) were dissolved in 100 ml of hydrochloric acid having a density of 1.19 g/ml, transferred to a 1000 ml volumetric flask and made up to the calibration mark. The solution contained 500 mg of platinum and corresponds to 500 Hazen units.

50±0.1 g of caprolactam were dissolved in 50 ml of distilled water in a 250 ml conical flask. The solution was thoroughly mixed and left to stand until the air bubbles vanished.

The two cells were filled with distilled water and placed in the measuring and reference beam path and the spectrophotometer was adjusted to A=0.000 at λ=λ390 nm. The distilled water was then removed from the sample cell, which was filled with the caprolactam solution. The absorbance A of this solution was measured once again at λ=390 nm, against the reference cell containing distilled water.

The color number in Hazen units or APHA units according to the platinum-cobalt scale was calculated using the formula:

Color number=150×$A_{390}$ $A_{390}$ is the absorbance of the caprolactam solution at λ=390 nm in a cell of length l=5 cm. 150 is the factor for calculating the APHA (Hazen) units.

COMPARATIVE EXAMPLE

The abovementioned example was repeated, except that no sulfuric acid was added in the first distillation (distillation in the acidic medium in the abovementioned example).

The main product of the second distillation carried out under alkaline conditions consisted of a caprolactam having the following quality characteristics

| | |
|---|---|
| Permanganate absorption number | 12 |
| Absorbance [1 cm cell/290 nm] of a 50% strength by weight aqueous solution | 0.16 |
| Volatile bases [meq/kg] | 0.3 |
| Free bases [meq/kg] | 2.8 |
| Octahydrophenazine content [mg/kg] | 1 |
| APHA color number | 6 |

We claim:

1. A process for recovering caprolactam from oligomers or polymers of caprolactam by cleavage of oligomers or polymers of caprolactam and subsequent working up by distillation of the caprolactam obtained in the cleavage, which comprises
   (a) cleaving oligomers or polymers of caprolactam to obtain an aqueous reaction mixture which contains caprolactam,
   (b) removing water from the reaction mixture obtained under (a) to obtain a residue,
   (c) distilling the residue obtained under (b) in an acidic medium and
   (d) then distilling distillate obtained in (c) in an alkaline medium to obtain caprolactam, or
   (c') distilling the residue obtained under (b) in an alkaline medium and
   (d') then distilling distillate obtained in (c') in an acidic medium to obtain caprolactam;

wherein forerunnings are taken off in the distillation in the acidic or alkaline medium and are separated by distillation into a low-boiling fraction, which is fed to an incineration plant, and a bottom fraction, which is recycled to the distillation (c) or (d') in acidic medium; and wherein residue obtained in the distillation in the alkaline medium is separated by distillation and distillate obtained here in (c') being recycled to the distillation (d') in the acidic medium.

2. The process of claim 1, wherein the aqueous reaction mixture is treated with lime, oxidizing agents or active carbon directly after the cleavage to form a reaction mixture of a solid component and a liquid phase.

3. A process of claim 2, wherein, after the treatment with lime, oxidizing agents or active carbon, the solid component is separated off and water is removed from the liquid phase.

4. The process of claim 1, wherein the distillation in the acidic medium is carried out in the presence of sulfuric acid and wherein the residue obtained in the distillation is fed to a cleavage sulfuric acid plant for incineration.

5. The process of claim 1, wherein the residue obtained in stage (b) is distilled in an acidic medium and the distilate obtained in (c) is distilled in a alkaline medium to obtain caprolactam.

6. The process of claim 1, wherein the residue obtained in stage (b) is distilled in an alkaline medium and thereafter the distilate obtained in the alkaline medium is distilled in an acidic medium to obtain caprolactam.

* * * * *